(12) United States Patent
Rohlfing et al.

(10) Patent No.: US 11,096,735 B2
(45) Date of Patent: Aug. 24, 2021

(54) SURGICAL INSTRUMENTS AND METHODS

(71) Applicant: Warsaw Orthopedic, Inc., Warsaw, IN (US)

(72) Inventors: Alexander J. Rohlfing, St Louis, MO (US); Jason M. May, Collierville, TN (US); William Alan Rezach, Covington, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 223 days.

(21) Appl. No.: 16/106,381

(22) Filed: Aug. 21, 2018

(65) Prior Publication Data

US 2020/0060743 A1 Feb. 27, 2020

(51) Int. Cl.
| *A61B 17/88* | (2006.01) |
| *A61B 17/16* | (2006.01) |
| *A61F 2/46* | (2006.01) |
| *A61B 90/00* | (2016.01) |

(52) U.S. Cl.
CPC ...... *A61B 17/8875* (2013.01); *A61B 17/1671* (2013.01); *A61F 2/4611* (2013.01); *A61B 2090/0811* (2016.02); *A61F 2002/4627* (2013.01)

(58) Field of Classification Search
CPC ............ A61B 17/8875; A61B 17/8877; A61B 17/888; A61B 17/8886; A61B 17/8888; A61B 17/8605; A61B 17/861; A61B 17/8615; A61B 17/1671; A61F 2/4611
USPC ...................................................... 606/104
See application file for complete search history.

(56) References Cited

U.S. PATENT DOCUMENTS

| 3,134,290 | A | 5/1964 | Jentoft |
| 4,215,600 | A | 8/1980 | Kesselman |
| 4,838,264 | A | 6/1989 | Bremer et al. |
| 5,368,480 | A | 11/1994 | Balfour et al. |
| 5,713,705 | A | 2/1998 | Grunbichler |
| 5,941,885 | A | 8/1999 | Jackson |
| 6,308,598 | B1 | 10/2001 | O'Neil |
| 6,530,896 | B1 | 3/2003 | Elliott |
| 7,127,955 | B2 | 10/2006 | Bondhus et al. |
| 7,144,252 | B2 | 12/2006 | Walton |
| 7,159,494 | B2 | 1/2007 | Jamnia et al. |
| 7,243,580 | B2 | 7/2007 | Frazee |
| 7,299,725 | B2 | 11/2007 | Helstern et al. |

(Continued)

FOREIGN PATENT DOCUMENTS

| FR | 2916820 A3 * | 12/2008 | ......... A61B 17/8875 |
| FR | 2916820 A3 | 12/2008 | |

OTHER PUBLICATIONS

FR2916820A3 translation attached (Year: 2008).*
European Search Report—EP 19 19 0041—dated Jan. 22, 2020 European Patent Office 80298 Munich Germany.

*Primary Examiner* — Si Ming Ku
(74) *Attorney, Agent, or Firm* — Sorell, Lenna & Schmidt, LLP

(57) ABSTRACT

A surgical instrument for implanting a bone fastener is provided. The surgical instrument comprises an elongated body having a frangible region and a distal end adjacent to the frangible region. The distal end of the surgical instrument is configured to engage the bone fastener. The bone fastener is less frangible than the frangible region of the elongated body of the surgical instrument. Kits and methods are also disclosed.

16 Claims, 9 Drawing Sheets

(56) References Cited

U.S. PATENT DOCUMENTS

| | | | |
|---|---|---|---|
| 8,028,608 B2 * | 10/2011 | Sixto, Jr. | ............ B25B 23/0042 |
| | | | 81/471 |
| 9,044,286 B2 | 6/2015 | O'Neil et al. | |
| 2007/0106283 A1 | 5/2007 | Garcia | |
| 2013/0012949 A1 | 1/2013 | Fallin | |
| 2013/0184759 A1 | 7/2013 | Rinehart | |
| 2016/0324562 A1 * | 11/2016 | Baker | .................... B22F 3/225 |
| 2018/0153599 A1 * | 6/2018 | Daly | ................. A61B 17/8605 |

* cited by examiner

SURGICAL INSTRUMENTS AND METHODS

TECHNICAL FIELD

The present disclosure generally relates to a surgical instrument for implanting a bone fastener. The surgical instrument includes an elongated body having a frangible region and a distal end adjacent to the frangible region. The surgical instrument is intended to be inspected at the frangible region by a user before or during a procedure to help prevent instrument failure.

BACKGROUND

Hundreds of thousands of spinal surgeries are performed throughout the world every year and this number continues to rise. Non-surgical treatments, such as medication, rehabilitation and exercise can be effective, however, they may fail to relieve the symptoms associated with particular spinal disorders and therefore, surgery appears to be a desirable option. Surgical treatment of certain spinal disorders includes correction, fusion, fixation, discectomy, laminectomy and implantable prosthetics. As part of these surgical treatments, spinal constructs, which include implants such as bone fasteners, connectors, plates and vertebral rods are often used to provide stability to a treated region.

During these surgical treatments, various surgical instruments can be used, for example, to engage bone fasteners (e.g., bone screws) for attachment to the exterior of the vertebrae. When bone fasteners are implemented, a surgical instrument, such as a driver, can be employed. Unfortunately, when a certain amount of torque is applied to the surgical instrument, the surgical instrument and/or the bone fastener can break and fail, causing portions of the surgical instrument and/or the bone fastener to break or fragment into the treated region. This is particularly so for procedures in a confined surgical site, such as, the spine, for which surgical instruments can have narrow distal tips that can break. Portions of the surgical instrument can also remain attached to the bone fastener, making it difficult to remove. And if not removed immediately, the portions could drift in the body.

SUMMARY

New devices and methods are provided that incorporate a frangible region on a surgical instrument such as a driver, so that during use and when a predetermined torque is reached, the frangible region breaks and the broken portion of the elongated body can be easily removed. In some embodiments, the driver is engineered to break at a frangible region at a predetermined torque that is below an ultimate torque for the remainder of the instrument as well as the bone fastener so as to allow a broken piece to be removed at the frangible region when the predetermined torque is reached. In some embodiments, the surgical instrument provided comprises visual indicia at or near the frangible region that allows visual indication that the surgical instrument has undergone unwanted wear and tear that may lead to breaking at the frangible region. In this way, the device can be discarded or replaced.

In some embodiments, a surgical instrument is provided. The surgical instrument comprises an elongated body having a frangible region and a distal end adjacent to the frangible region. The distal end of the surgical instrument is configured to engage the bone fastener. The bone fastener is less frangible than the frangible region of the elongated body of the surgical instrument.

In some embodiments, a kit for implanting a bone fastener is provided. The kit comprises a surgical instrument comprising an elongated body having a frangible region and a distal end adjacent to the frangible region, the distal end of the surgical instrument configured to engage the bone fastener, the bone fastener being less frangible than the frangible region of the elongated body of the surgical instrument; and a bone fastener configured to engage the distal end of the surgical instrument.

In some embodiments, a method for implanting a bone fastener to a surgical site is provided. The method comprises engaging a distal end of a surgical instrument with the bone fastener so as to implant the bone fastener at the surgical site, the surgical instrument comprising an elongated body having a frangible region and the distal end adjacent to the frangible region, the distal end of the surgical instrument configured to engage the bone fastener, the bone fastener being less frangible than the frangible region of the elongated body of the surgical instrument.

While multiple embodiments are disclosed, still other embodiments of the present disclosure will become apparent to those skilled in the art from the following detailed description. As will be apparent, the disclosure is capable of modifications in various obvious aspects, all without departing from the spirit and scope of the present disclosure. Accordingly, the detailed description is to be regarded as illustrative in nature and not restrictive.

BRIEF DESCRIPTION OF THE FIGURES

In part, other aspects, features, benefits and advantages of the embodiments will be apparent with regard to the following description, appended claims and accompanying figures.

In FIG. 12, the first visual indicia and the second visual indicia are misaligned indicating plastic deformation of the driver and the driver should be replaced or discarded.

As shown in FIG. 13, when too much torque is applied to the instrument, the driver will break at the frangible region of the elongated body, and the broken portion of the driver can be removed from the surgical site. This will also prevent the driver from exceeding the ultimate torque limit for the head of the screw during implantation.

Figure 1:
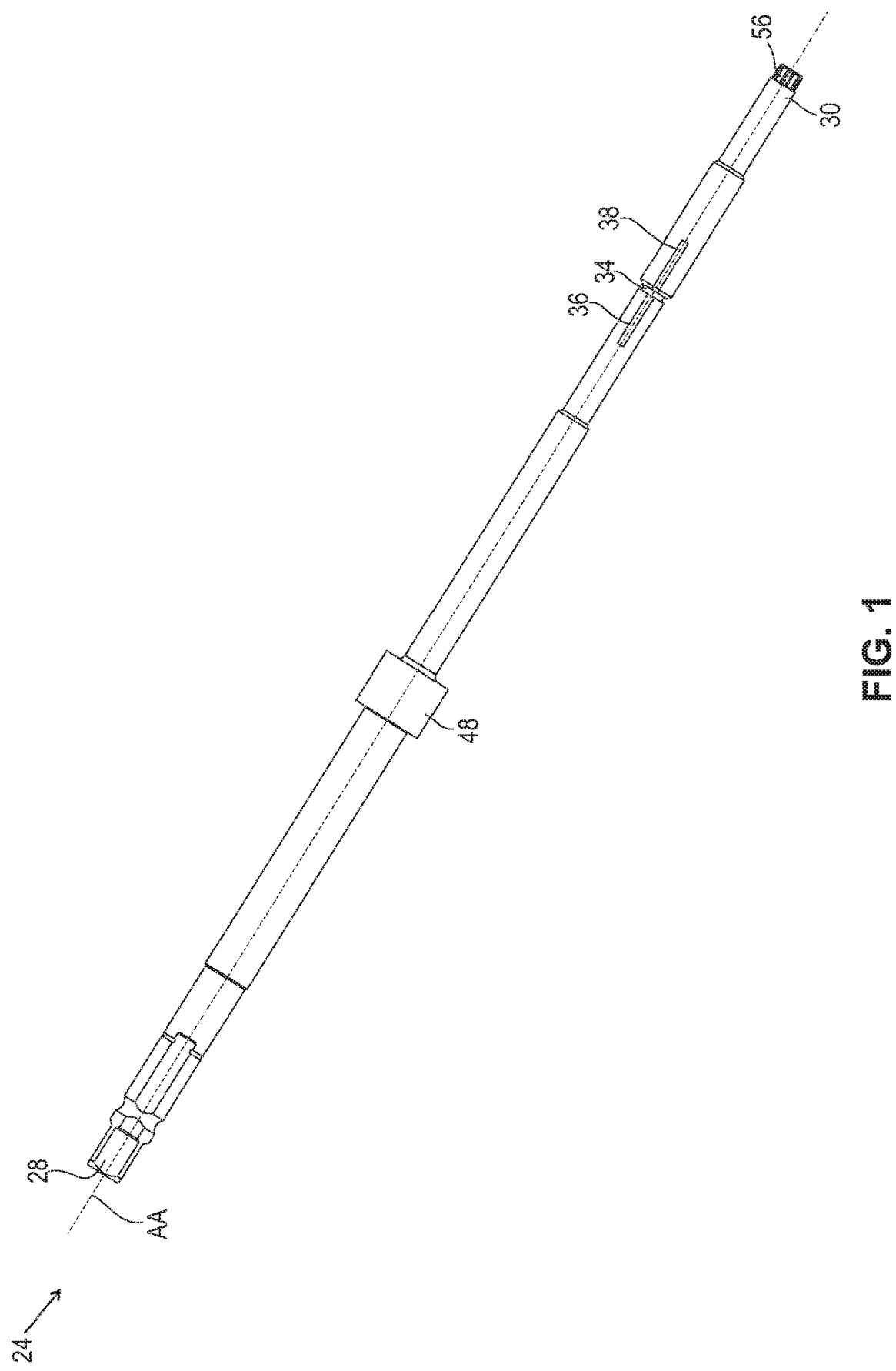
FIG. 1 is a perspective view of the elongated body of the surgical instrument having a frangible region and the first visual indicia and second visual indicia.

It is to be understood that the figures are not drawn to scale. Further, the relation between objects in a figure may not be to scale and may in fact have a reverse relationship as to size. The figures are intended to bring understanding and clarity to the structure of each object shown, and thus, some features may be exaggerated in order to illustrate a specific feature of a structure.

DETAILED DESCRIPTION

Definitions

It is noted that, as used in this specification and the appended claims, the singular forms "a," "an," and "the," include plural referents unless expressly and unequivocally limited to one referent.

The term "patient" refers to a biological system to which a treatment can be administered. A biological system can include, for example, an individual cell, a set of cells (e.g., a cell culture), an organ, or a tissue. Additionally, the term "patient" can refer to animals, including, without limitation, humans.

The terms "upper," "lower," "top," "bottom," "side," "proximal," "distal" and so forth have been used herein merely for convenience to describe the present invention and its parts as oriented in the drawings. It is to be understood, however, that these terms are in no way limiting to the disclosure since the dispensing systems described herein may obviously be disposed in different orientations when in use.

The terms "frangible region," "break-off," "shearing regions" or "shear," refers to a section of an instrument or implant that is designed to separate two or more sections from each other. The frangible region may be activated by different forms of energy including, for example, pressure, force, heat, torque and combinations thereof. Embodiment devices may contain one or more types of frangible regions.

The term "torque" refers to a twisting or turning force that tends to cause rotation around an axis, which can be a center of mass or a fixed point. In this disclosure, torque is measured in pounds per foot or newtons per meter (N-m). "Ultimate torque" includes the maximum amount of torque for the surgical instrument, which will not cause plastic deformation, shearing or breaking of the surgical instrument. The term "ultimate force" can be used analogously.

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention is an approximation; the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the disclosure, examples of which are illustrated in the accompanying figures. While the disclosure will be described in conjunction with the illustrated embodiments, it will be understood that they are not intended to limit the disclosure to those embodiments. On the contrary, the disclosure is intended to cover all alternatives, modifications, and equivalents that may be included within the disclosure as defined by the appended claims.

The headings below are not meant to limit the disclosure in any way; embodiments under any one heading may be used in conjunction with embodiments under any other heading.

Surgical Instrument

New devices and methods are provided that incorporate a frangible region on a surgical instrument such as a driver, so that during use and when a predetermined torque is reached, the frangible region breaks and the broken portion of the elongated body can be easily removed. In some embodiments, the driver is engineered to break at a frangible region at a predetermined torque that is below the ultimate torque for the remainder of the instrument as well as the bone fastener so as to allow a broken piece to be removed at the frangible region when the predetermined torque is reached. In some embodiments, the surgical instrument provided comprises visual indicia at or near the frangible region that allows visual indication that the surgical instrument has undergone unwanted wear and tear that may lead to breaking at the frangible region. In this way, the device can be discarded or replaced.

The surgical instrument can be any instrument used to implant a bone fastener. Suitable instruments include drivers, drill bits, rods, burrs or the like. Referring to FIGS. 1-13, a surgical instrument is shown, such as a driver 20 (FIG. 1) for implanting a bone fastener 22 (FIGS. 10-13). The driver can be similar to the drivers described and fully disclosed in U.S. application Ser. Nos. 15/899,081 and 15/899,103, of which is assigned to Warsaw Orthopedic, Inc. and incorporated herein by reference. The driver includes an elongated body 24 that is configured for movable engagement with an outer sleeve 26 (FIGS. 10-13) for implanting the bone fastener, as described herein. The elongated body includes a proximal end 28, a distal end 30 and a longitudinal axis AA disposed therebetween, as shown in FIG. 1. Visual indicia 36 and 38 are shown, by way of example, in an aligned position relative to axis AA. These indicia are disposed adjacent to a relatively frangible region 34. The frangible region is not weak or fragile, per se, but rather is, in one manner or another, not as strong as portions of the driver adjacent the frangible region 34.

Figure 12:
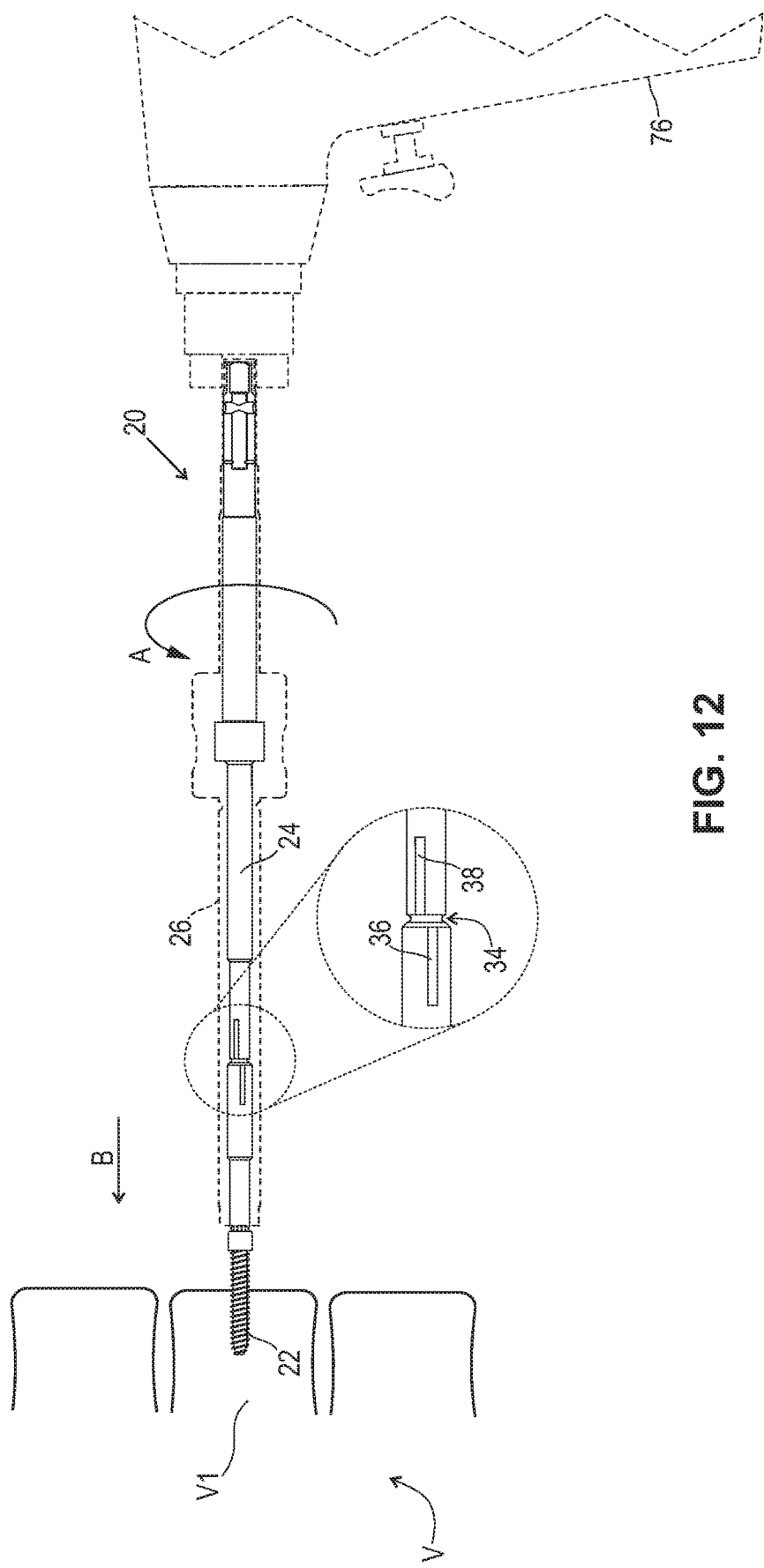
FIG. 12 is a partially phantom side view of the surgical instrument, such as the driver of FIG. 3 where the distal end of the driver is shown engaging a head of a bone fastener so as to implant the bone fastener at a surgical site, such as a vertebra V1.

Before, during or after use of the driver 20, the user can view the driver, and if the visible indicia are misaligned, as shown by way of example in FIG. 12, the driver has reached a maximum point of wear and tear and can be discarded as subsequent use may cause the driver to break at the frangible region 34. Even if the user does not detect the misalignment of the indicia, upon use of the driver, the frangible region, if broken, will allow the user to remove a portion of the driver that extends from the frangible region to the distal end from the surgical site. In this way, the driver has an additional safety feature. This will also ensure that the bone fastener will not fragment when greater than the ultimate torque is reached for the driver. This is also a safety feature.

It will be understood that proximal end 28 can include a hexagonal or square geometry configured for engagement with a similarly shaped surgical tool. It is to be understood that the proximal end can include any shaped geometry and is not limited to hexagonal or square. The proximal end can engage with an oscillating tool, such as, for example, a drill, a ratchet or other rotatable tools to facilitate rotation of the driver for implantation of the bone fastener. The distal end includes a tip 32 (FIG. 2) that is configured for engagement with the bone fastener, as described herein. The distal end of the elongated body comprises a second frangible region, as will be described herein.

The elongated body 24 includes the frangible region 34 that is adjacent to the distal end. The frangible region can be a shear ring that is configured to break during implantation of the bone fastener when a predetermined amount of torque and/or force, less than an ultimate torque or force for the balance of the driver, is applied to the driver. When the frangible region breaks, a certain amount of the distal end of the instrument is left engaged with the bone fastener and extends outside of the surgical site (e.g., the patient's body), as described herein. Breaking the elongated body at the frangible region ensures that above the ultimate torque capacity for the distal end of the driver and the bone fastener is not reached as the frangible region will break before the ultimate torque for the distal end of the driver and the bone fastener is reached. Further when the elongated body breaks at the frangible region, it allows a user to easily extract the distal end of the elongated body from the bone fastener. It is to be understood by those of ordinary skill in the art that the frangible region is not required to break, fragment, tear or fracture during use of the driver and that the frangible region can remain intact if a predetermined torque is not reached.

The amount of predetermined torque required to break the frangible region can be in some embodiments, from about 18.5 to about 20 newton meters (N-m). In some embodiments, the amount of predetermined torque is from about 18.5, 18.6, 18.7, 18.8, 18.9, 19, 19.1, 19.2, 19.3, 19.4, 19.5, 19.6, 19.7, 19.8, 19.9 to about 20 N-m. The predetermined torque of the frangible region is less than the ultimate torque of the remainder of the elongated body and the bone fastener.

Figure 2:
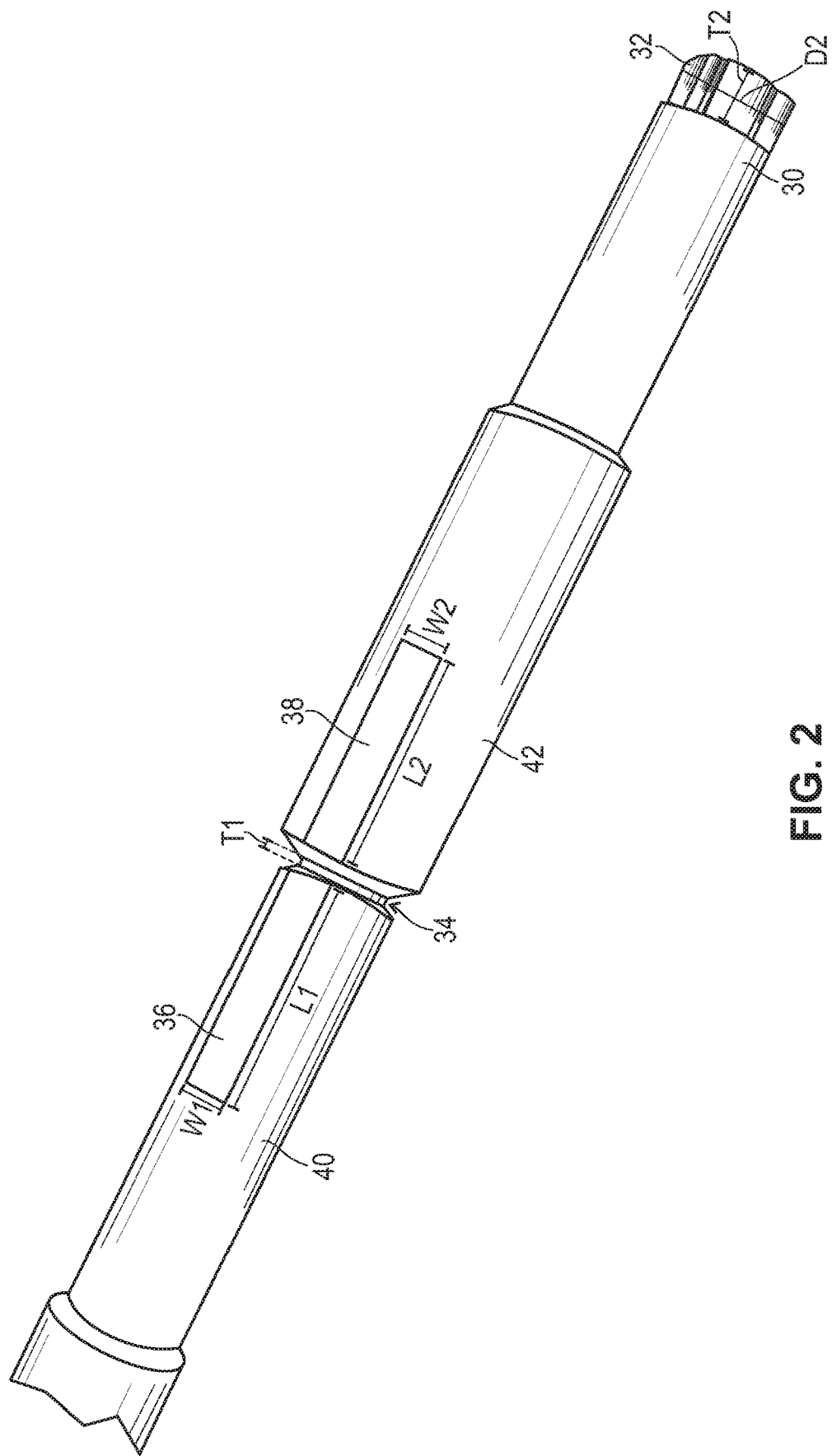
FIG. 2 is an enlarged perspective view of the frangible region, the first visual indicia and second visual indicia of the elongated body.

In some embodiments, the frangible region is positioned about 1 to about 3.5 inches from the distal end of the elongated body, as shown in FIG. 2. In some embodiments, the frangible region is positioned from about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4 to about 3.5 inches from the distal end of the elongated body. In this way, when or if the frangible region breaks, it can be easily removed from the surgical site and this will prevent unwanted broken pieces of instrument at the surgical site and unwanted migration of these pieces.

Figure 5:
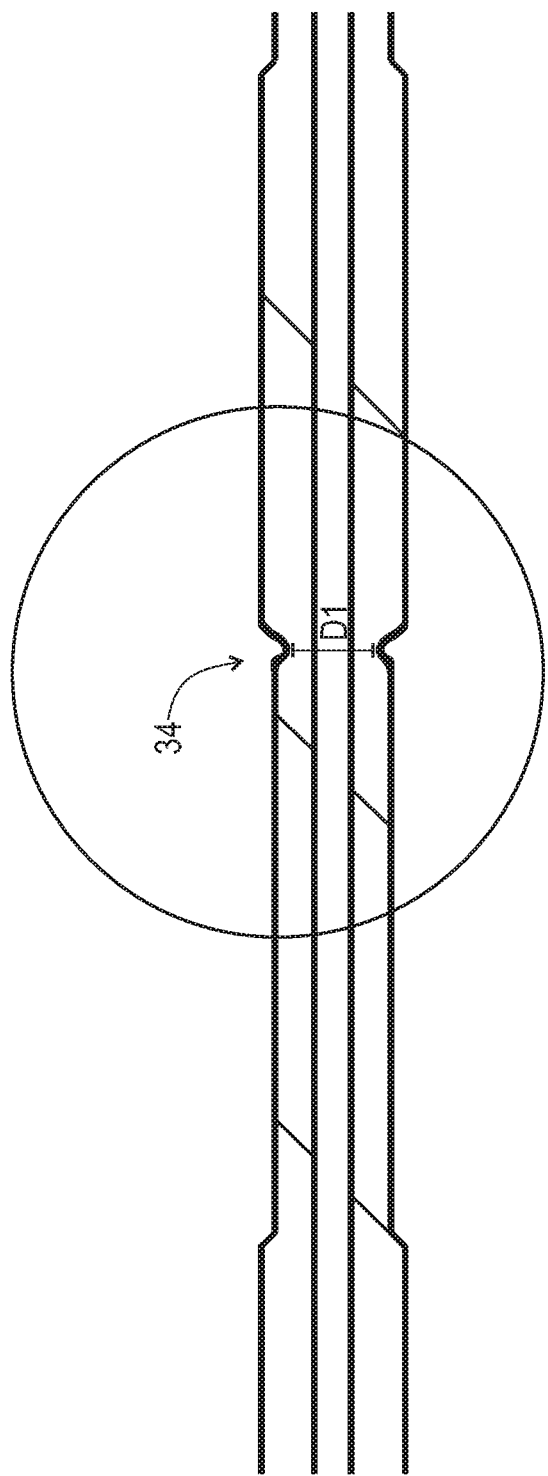
FIG. 5 is an enlarged cross sectional side view of a groove shaped frangible region located at a discrete region of the elongated body.
Figure 6:
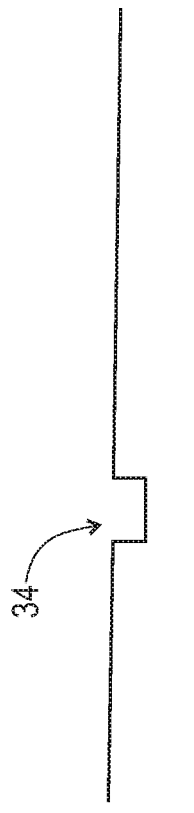
FIG. 6 is a side view of an embodiment of a beveled shaped frangible region of the elongated body.
Figure 7:
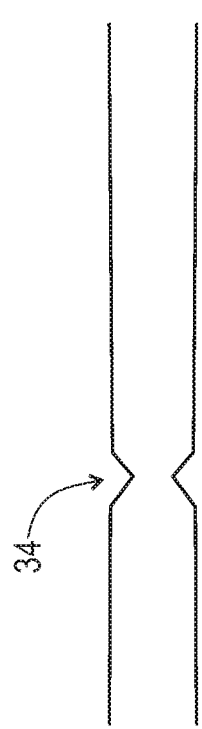
FIG. 7 is a side view of an embodiment of a square shaped frangible region of the elongated body.
Figure 8:
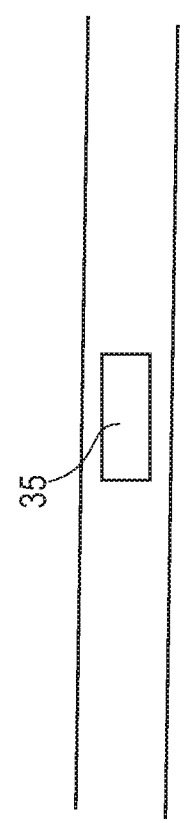
FIG. 8 is a side view of an embodiment of a semi-circular shaped frangible region of the elongated body.

In some embodiments, the frangible region has a diameter D1, as shown in FIG. 5 that is less than a diameter D2 of the distal end of the elongated body, as shown in FIG. 2. Diameter D1 can be from about 4 mm to about 20 mm. In some embodiments, diameter D1 can be from about 4, 5, 6, 7, 8, 9, 10, 11, 12, 13, 14, 15, 16, 17, 18, 19 to about 20 mm. Diameter D2 can be from about 6 mm to about 24 mm. In some embodiments, diameter D2 can be from about 6, 7, 8, 9, 10, 11, 12, 13, 14, 15, 16, 17, 18, 19, 20, 21, 22, 23 to about 24 mm.

The frangible region can have a certain thickness T1, as shown in FIG. 2. The thickness can be from about 2 mm to about 10 mm. In some embodiments, the thickness T1 can be from about 2, 3, 4, 5, 6, 7, 8, 9 to about 10 mm. In various embodiments, thickness T1 is not as thick as a thickness T2 of the distal end of the elongated body. Thickness T2 can be from about 4 to about 18 mm. In some embodiments, thickness T2 can be from about 4, 5, 6, 7, 8, 9, 10, 11, 12, 13, 14, 15, 16, 17 to about 18 mm. Thickness T1 is the least thick area on the elongated body. Thickness T2 is less thick than other sections of the elongated body but is thicker than T1.

In some embodiments, the frangible region can be a shear ring, as shown in FIGS. 1 and 2. Alternate geometries as shown in FIGS. 5-8 can be used to create the frangible region feature. For example, the frangible region can be circumferential (e.g., a shear ring) relative to the elongated body but can also be at least 1, 2, 3, 4, 5, 6 or more indents that are variously shaped. In some embodiments, the frangible region is one or more indents or tabs that are beveled (FIG. 6), concave, grooved (FIG. 5), dimpled, squared (FIG. 7), semi-circular (FIG. 8) or a combination thereof.

Figure 9:
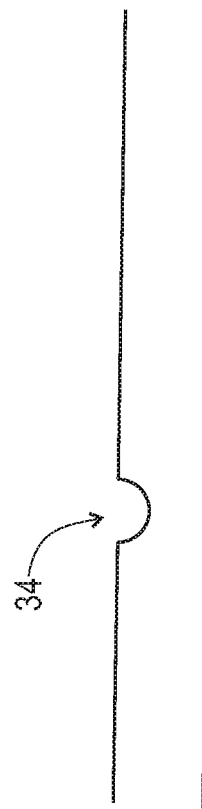
FIG. 9 is a side view of an embodiment of a frangible region that is a hollow portion within the elongated body.

In various embodiments, the frangible region can also be a hollow portion 35 within the elongated body, as shown in FIG. 9. For example, the elongated body can be solid except at the hollow portion such that the hollow portion is frangible relative to the remainder of the elongated body. In some embodiments, the hollow portion can be variously sized and dimensioned. In various embodiments, the hollow portion can be rectangular, square, triangular or disc shaped.

The frangible region can be monolithic with the elongated body and can be machined into the elongated body during manufacture. The frangible region can also be made from the same or different material as the elongated body. In some embodiments, the frangible region can be made from a homogenous material or heterogeneously fabricated from different materials than the elongated body, and/or alternately be formed from a material having a greater degree, characteristic or attribute of plastic deformability, frangible property and/or break away quality than the elongated body to facilitate fracture and separation from the elongated body.

The elongated body includes indicia, such as a first visual indicia 36 and a second visual indicia 38. The first visual indicia is located on a first portion 40 of the elongated body that is adjacent to, and in various embodiments is contacting, the frangible region of the elongated body. The second visual indicia is located on a second portion 42 of the elongated body that is adjacent to, and in various embodiments is also contacting, the frangible region. The second visual indicia aligns in some manner with the first visual indicia, as shown in FIG. 2. In various embodiments, the two indicia include two co-linear lines, but they can align in other ways, such as by being formed in the shape of arrows or chevrons having points aligned directly across from each other.

It is to be understood that at least the second portion of the elongated body is the portion that can break off at the frangible region. The first visual indicia and the second visual indicia indicate plastic deformation at the frangible region. For example, when a certain amount of torque is applied that is approaching the predetermined torque described above, the frangible region will start to deform before it breaks, as shown in FIG. 12. In various embodiments, when plastic deformation initiates, the visual indicia will become misaligned, indicating an alert to the user that the driver is about to fail or break. The user can then halt use of the driver before instrument failure occurs. Further, when misalignment occurs, it is an indication that the engagement between the distal end of the driver and the head of the bone fastener is not in ideal engagement. Therefore, the bone fastener can be checked as well for potential plastic deformation.

The first visual indicia and the second visual indicia can be any marker that allows the user to detect misalignment. The first visual indicia and the second visual indicia can be disposed adjacent to or can contact the frangible region. The first visual indicia and the second visual indicia can be, for example, laser markings that are linear and run longitudinal on a surface of the first portion and the second portion of the elongated body. The laser markings can be machined or etched into the surface of the first portion and the second portion. Alternatively, the first visual indicia and the second visual indicia can be strips or adhesive labels/stickers fabricated from a polymeric material. The first visual indicia and the second visual indicia can be a certain color such as blue, orange, red, pink, purple, green, yellow, black and/or white.

In some embodiments, the visual indicia can include markings that comprise a plurality of spaced apart graduations. In some embodiments, the indicia can include human readable visual indicia, such as, for example, a label, color coding as described above, or alphanumeric characters. In some embodiments, the indicia can include human readable tactile indicia, such as, for example, raised portions or lowered portions. In some embodiments, indicia is a printed or written item in combination with a slot or groove, whereby the printed or written item is placed in the slot or groove.

The first visual indicia may be a certain length L1 and the second visual indicia may be a certain length L2. For example, lengths L1 and L2 can be from about 4 mm to about 20 mm. In some embodiments, lengths L1 and L2 can be the same or different and can be from about 4, 5, 6, 7, 8, 9, 10, 11, 12, 13, 14, 15, 16, 17, 18, 19 to about 20 mm. The first visual indicia may be a certain width W1 and the second visual indicia may be a certain width W2. For example, widths W1 and W2 can be from about 2 to about 10 mm. In some embodiments, widths W1 and W2 can be the same or different and can be from about 2, 3, 4, 5, 6, 7, 8, 9 to about 10 mm.

Figure 3:
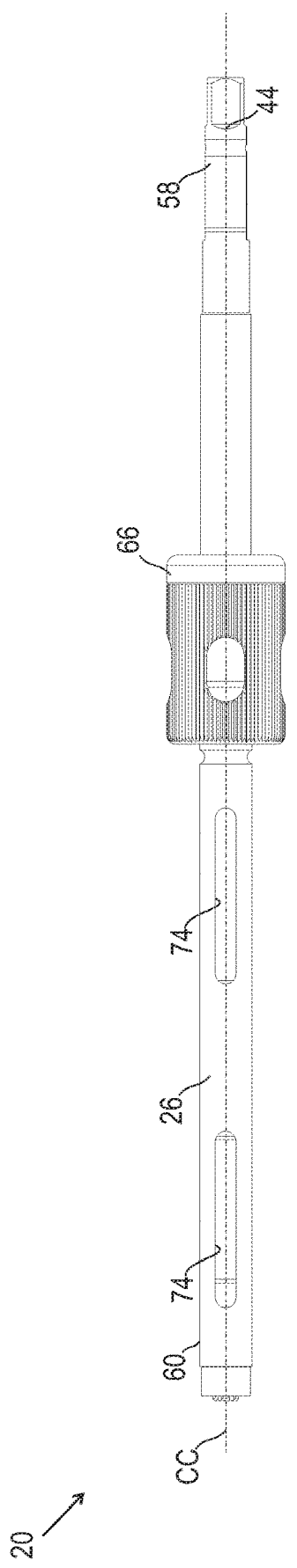
FIG. 3 is a side view of the surgical instrument, specifically in the form of a driver. The driver comprises the elongated body and an outer sleeve.
Figure 4:
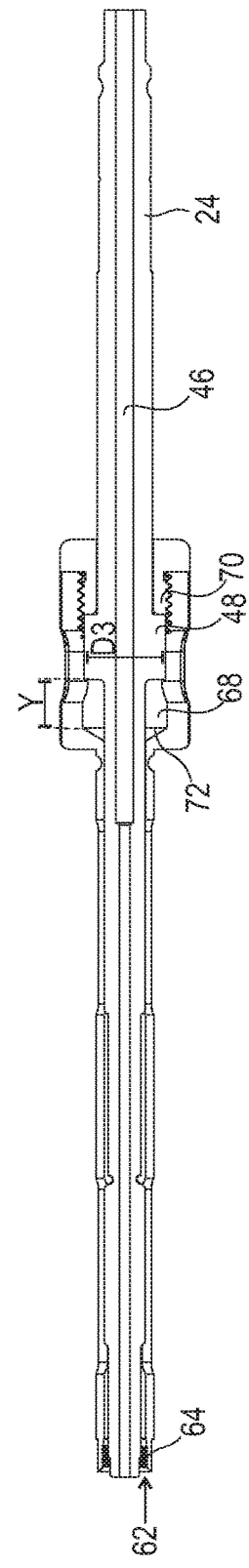
FIG. 4 is cross sectional side view of the surgical instrument of FIG. 3 having an outer sleeve.

In some embodiments, as shown in FIGS. 3 and 4, the elongated body can include an opening 44 at the proximal end. The opening is the entrance to a channel 46 such that the elongated body can engage bone fasteners of different sizes and shapes. In some embodiments, the channel and/or the elongated body may have various cross-section configurations, such as, for example, oval, oblong, triangular, rectangular, square, polygonal, irregular, uniform, non-uniform, variable, tubular and/or tapered.

The elongated body includes, in some embodiments, a circumferential flange 48, as shown in FIG. 1 that is configured for engagement with a portion of an outer sleeve, as described herein, for implanting the bone fastener. The circumferential flange can have a smooth surface or a threaded surface to facilitate rotational movement with an inner portion of an outer sleeve, as described herein. As shown in FIG. 4, the circumferential flange can have a diameter D3. Diameter D3 is greater than diameters D1 and D2. The circumferential flange is proximal to the frangible region.

Figure 10:
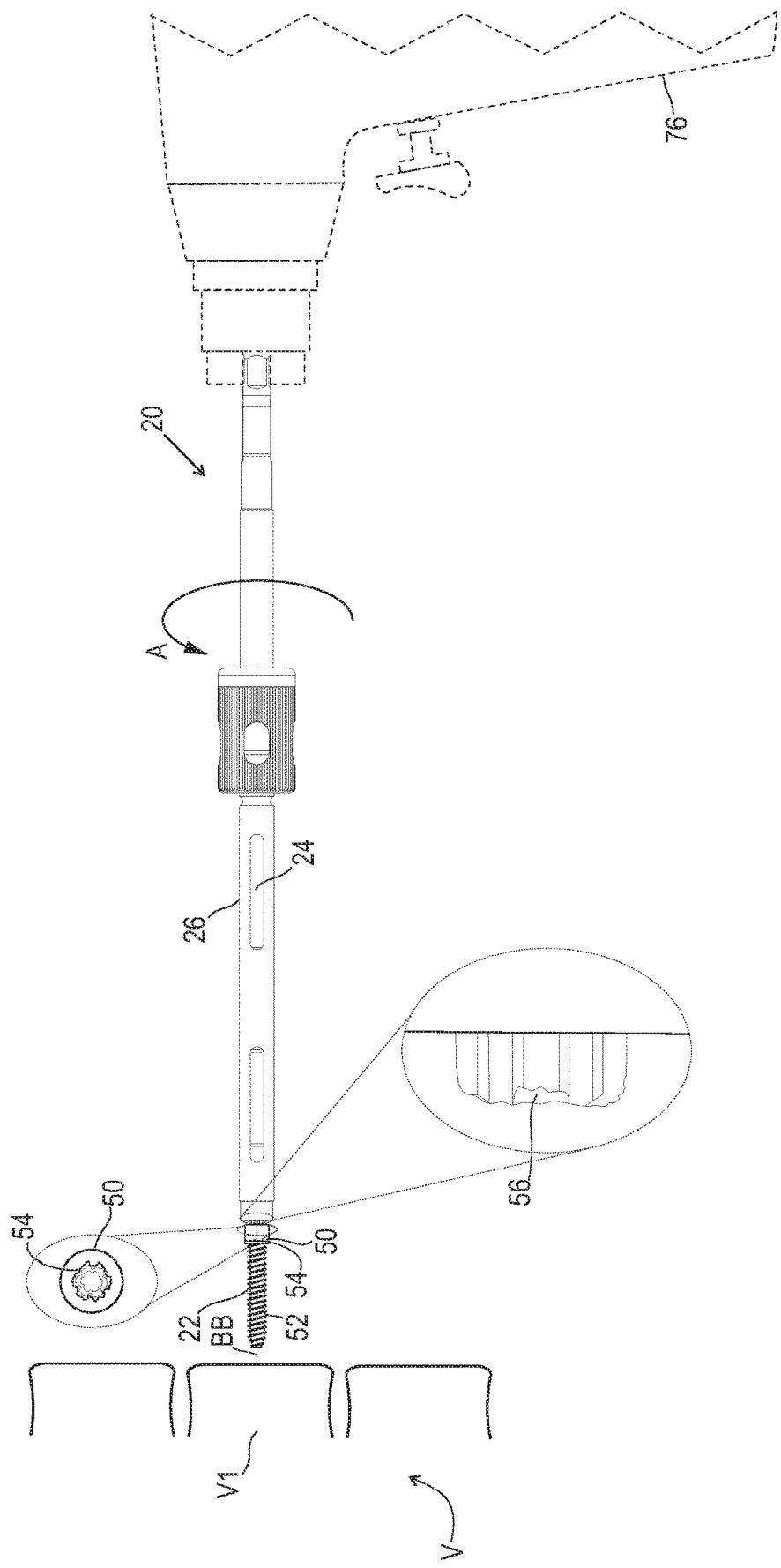
FIG. 10 is a side view of the surgical instrument, such as the driver of FIG. 3 where the distal end of the driver is shown engaging a head of a bone fastener so as to implant the bone fastener at a surgical site, such as a vertebra V1. A first frangible region located in the head of the bone fastener is shown enlarged and stripped so as to show frangibility, and a second frangible region located at the distal end of the driver is shown enlarged and damaged to show frangibility.

As described above, the distal end of the elongated body is configured for engagement with bone fastener 22, shown as a bone screw. The bone fastener includes a head 50, a shaft 52 and a longitudinal axis BB disposed therebetween, as shown in FIG. 10. The head includes at least a first frangible region 54. The first frangible region of the bone fastener is less frangible than the frangible region of the elongated body of the driver. The ultimate torque of the first frangible region of the bone fastener is more than or greater than the predetermined torque of the frangible region. Therefore, if the predetermined torque is reached at the frangible region, the driver will break without deforming the bone fastener at its frangible portion because the frangible region of the driver will break well before the ultimate torque is reached for the bone fastener or other parts of the driver particularly the distal end or tip of the driver. If the driver breaks, the frangible region will be located at a discrete region spaced a distance away from the surgical site where it can be removed. For example, the ultimate torque of the first frangible region can be greater than 20 N-m.

In some embodiments, the tip of the elongated body can include a socket configured for a mating engagement with the head of the bone fastener. The shaft of the bone fastener is configured for penetrating tissue. In some embodiments, at least a portion of the shaft has a generally cylindrical shape, and thus a generally circular cross-sectional configuration. The shaft may also taper, such as by narrowing in width approaching a tip of the shaft. The shaft includes an outer surface having an external thread form, as shown in FIG. 10. In some embodiments, the external thread form may include a single thread or a plurality of discrete threads. In some embodiments, other engaging structures may be located on the shaft, such as, for example, a nail configuration, barbs, expanding elements, raised elements and/or spikes to facilitate engagement of the shaft with tissue.

In some embodiments, all or at least a portion of the shaft of the bone fastener has any of various cross-sectional configurations, such as, for example, oval, oblong, triangular, square, polygonal, irregular, uniform, non-uniform, offset, staggered, undulating, arcuate, variable and/or tapered. In some embodiments, the outer surface of the shaft may include one or a plurality of openings. In some embodiments, all or only a portion of the outer surface of the shaft may have any of various surface configurations to enhance fixation with tissue, such as, for example, rough, arcuate, undulating, mesh, porous, semi-porous, dimpled and/or textured. In some embodiments, all or only a portion of the shaft may be disposed at alternate orientations, relative to its longitudinal axis, such as, for example, transverse, perpendicular and/or other angular orientations such as acute or obtuse, co-axial and/or may be offset or staggered. In some embodiments, all or only a portion of the shaft may be cannulated.

The bone fastener can be employed with a single vertebral level or a plurality of vertebral levels. In some embodiments, the bone fasteners may be engaged with vertebrae in various orientations, such as, for example, series, parallel, offset, staggered and/or alternate vertebral levels. In some embodiments, the bone fasteners may include one or a plurality of multi-axial screws, sagittal angulation screws, pedicle screws, mono-axial screws, uni-planar screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

The distal end of the elongated body comprises a second frangible region 56 in various embodiments. In some cases, the second frangible region is all or a portion of the tip, and the second frangible region is less frangible than frangible region 34, but is more frangible than first frangible region 54 of the bone fastener. In various embodiments, when the second frangible region is all or a portion of the tip, the tip geometry and/or axial grooves on the tip make it frangible (FIG. 10). When all or a portion of the tip is frangible, fragments of the tip can break off when ultimate torque for the second frangible region is reached. In various embodiments, the first frangible region of the head of the bone fastener is frangible due to the socket geometry, socket dimensions and/or the material that the head of the bone fastener is made from (FIG. 10). When the head of the bone fastener is frangible, fragments of the head can break off when ultimate torque for the first frangible region is reached. For example, as shown in FIG. 10, the socket can shear when ultimate torque for the first frangible region is reached. The ultimate torque of the second frangible region is more than or greater than the predetermined torque of the frangible region, but in some embodiments, the ultimate torque of the second frangible region is less than the ultimate torque of the first frangible region of the bone fastener. For example, the ultimate torque of the second frangible region is greater than 20 N-m. It is to be understood that the frangible region of the elongated body, the first frangible region of the bone fastener and/or the second frangible region of the distal end of the elongated body deforms or breaks at a predetermined torque or above an ultimate torque for those regions.

As described above, the driver can include an outer sleeve 26 that is configured for movable engagement with the elongated body for implanting the bone fastener. The outer sleeve is movable relative to the elongated body to engage the head of the bone fastener in a co-axial, capture orientation to implant the bone fastener into a vertebra V1. The outer sleeve can partially enclose the elongated body. The outer sleeve includes a proximal end 58, a distal end 60 and a longitudinal axis CC disposed therebetween. Longitudinal axes AA of the elongated body, BB of the bone fastener and CC of the outer sleeve are in co-axial alignment.

The distal end of the outer sleeve is disposed in a spaced apart relation with the distal end of the elongated body to define a cavity 62, as shown in FIG. 4. The cavity is configured for disposal of the head of the bone fastener. The distal end includes an inner surface that defines a threaded portion 64. The threaded portion is configured for engagement with a portion or a threaded portion of the bone fastener to pull and/or draw the bone fastener axially into the cavity and into engagement with the distal end of the elongated body. The outer sleeve is mounted with the elongated body for axial translation relative to the elongated body. The outer sleeve is translatable relative to the elongated body to capture the bone fastener with the driver. The outer sleeve pulls and/or draws the head of the bone fastener into the cavity of the distal end of the outer sleeve for capture of the bone fastener.

Figure 11:
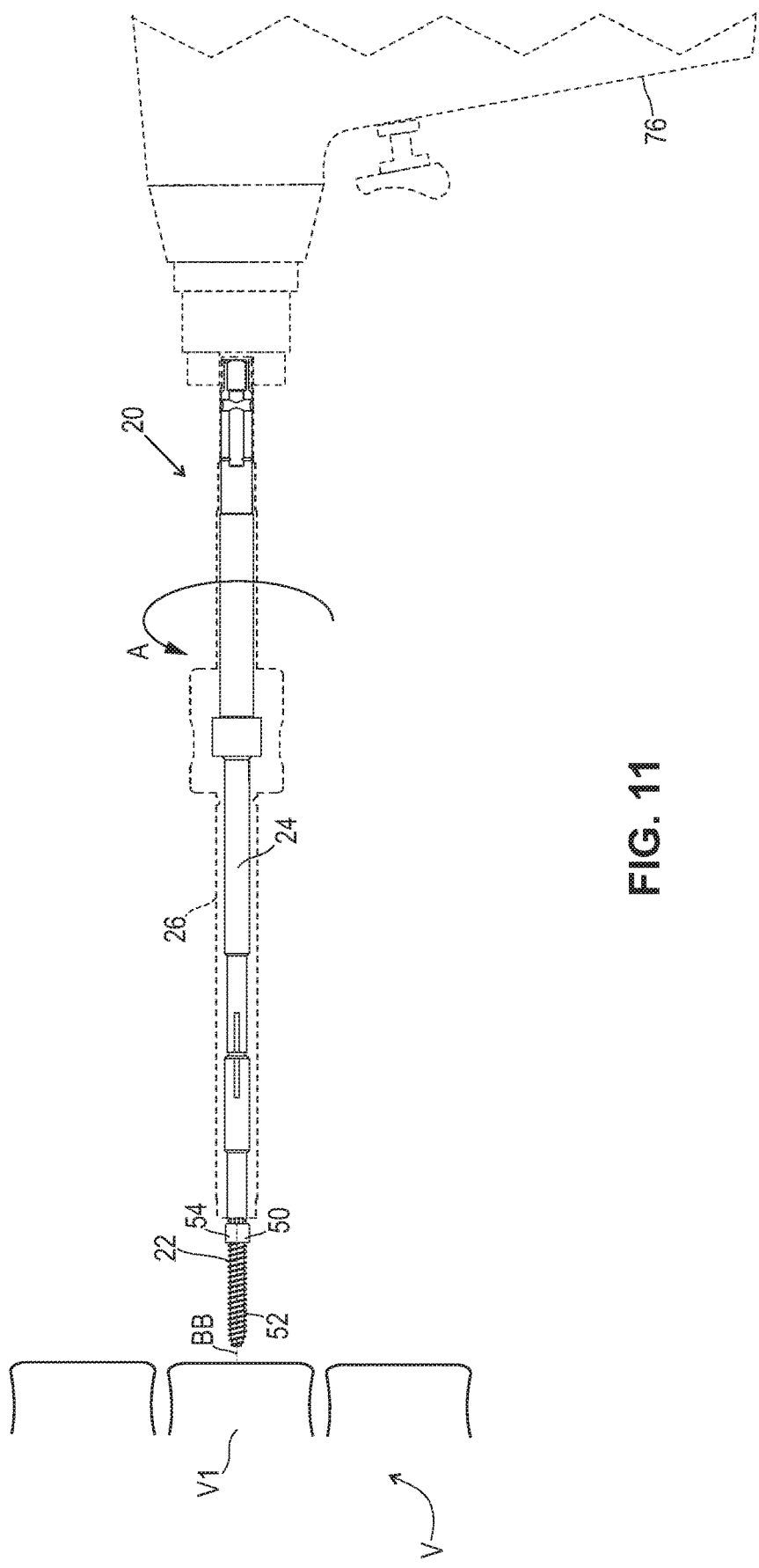
FIG. 11 is a partially phantom side view of the surgical instrument, such as the driver of FIG. 3 where the distal end of the driver is shown engaging a head of a bone fastener so as to implant the bone fastener at a surgical site, such as a vertebra V1.

The outer sleeve includes a gripping portion 66 configured for engagement with circumferential flange 48 of the elongated body. The gripping portion can be rotated, for example, in a clockwise direction, as shown by arrow A in FIG. 11. The gripping portion can be variously textured and made from various materials. The gripping portion includes at least one inner surface that defines a barrel 68. The barrel is configured for moveable disposal of the circumferential flange of the elongated body. The gripping portion includes a proximal limit 70 and a distal limit 72 of axial translation of the elongated body relative to the outer sleeve, as shown in FIG. 4. The circumferential flange is translatable a distance Y within the barrel between limits 70, 72. The circumferential flange is distally translatable to limit 72 so that the tip of the distal end of the elongated body extends beyond the distal end of the outer sleeve to facilitate engagement with the bone fastener, as shown in FIG. 11. The tip of the elongated body is connected with the bone fastener and the outer sleeve is threaded with an outer surface of the bone fastener, as described herein, such that the circumferential flange is proximally translatable to limit 70. Limit 70 resists and/or prevents the elongated body from further proximal translation by engagement of the circumferential flange with limit 70 and/or extends out of the threaded engagement between the outer sleeve and the bone fastener.

The outer sleeve includes one or more windows 74, as shown in FIG. 4 that correspond to the visual indicia and the frangible region such that the user is able to inspect the elongated body, in particular, the visual indicia and the frangible region. This can be done before and after use. The driver of the current application, therefore, provides safety features. The visual indicia can be inspected for misalignment before use and, the driver discarded. This will prevent unwanted fragments of the driver from entering into the surgical site and also will reduce the chance of driver failure and/or bone fastener failure by reaching torque greater than the ultimate torque of the driver and/or the bone fastener.

For example, when the outer sleeve engages the elongated body, the one or more windows expose the visual indicia and/or the frangible region for a user to determine whether the visual indicia are in alignment and/or whether the frangible region is about to break. The one or more windows can be variously configured and can be various sizes and shapes. For example, the one or more windows can be oval, rectangular, square, circular, or a combination thereof. The one or more windows can have straight or rounded edges. The one or more windows are sized in a manner that allows all or a portion of the indicia and/or the frangible region to be viewed by the user.

In some embodiments, the outer sleeve may have various cross-section configurations, such as, for example, oval, oblong, triangular, rectangular, square, polygonal, irregular, uniform, non-uniform, variable, tubular and/or tapered.

In operation and use, as shown in FIGS. 10-13, the driver is employed with a surgical procedure, such as, for example, a surgical treatment of an applicable condition or injury of an affected section of a spinal column and adjacent areas within a body. In some embodiments, the driver can be used in any surgical method or technique including open surgery, mini-open surgery, minimally invasive surgery and percutaneous surgical implantation, whereby vertebrae V is accessed, such as through a mini-incision, and possibly also via a sleeve (not shown) that provides a protected passageway to vertebrae V. Once access to the surgical site is obtained, the particular surgical procedure can be performed for treating the spine disorder.

An incision is made in the body of a patient and a cutting instrument (not shown) creates a surgical pathway. A preparation instrument (not shown) can be employed to prepare tissue surfaces of or surrounding vertebrae V, as well as for aspiration and irrigation of a surgical region.

Figure 13:
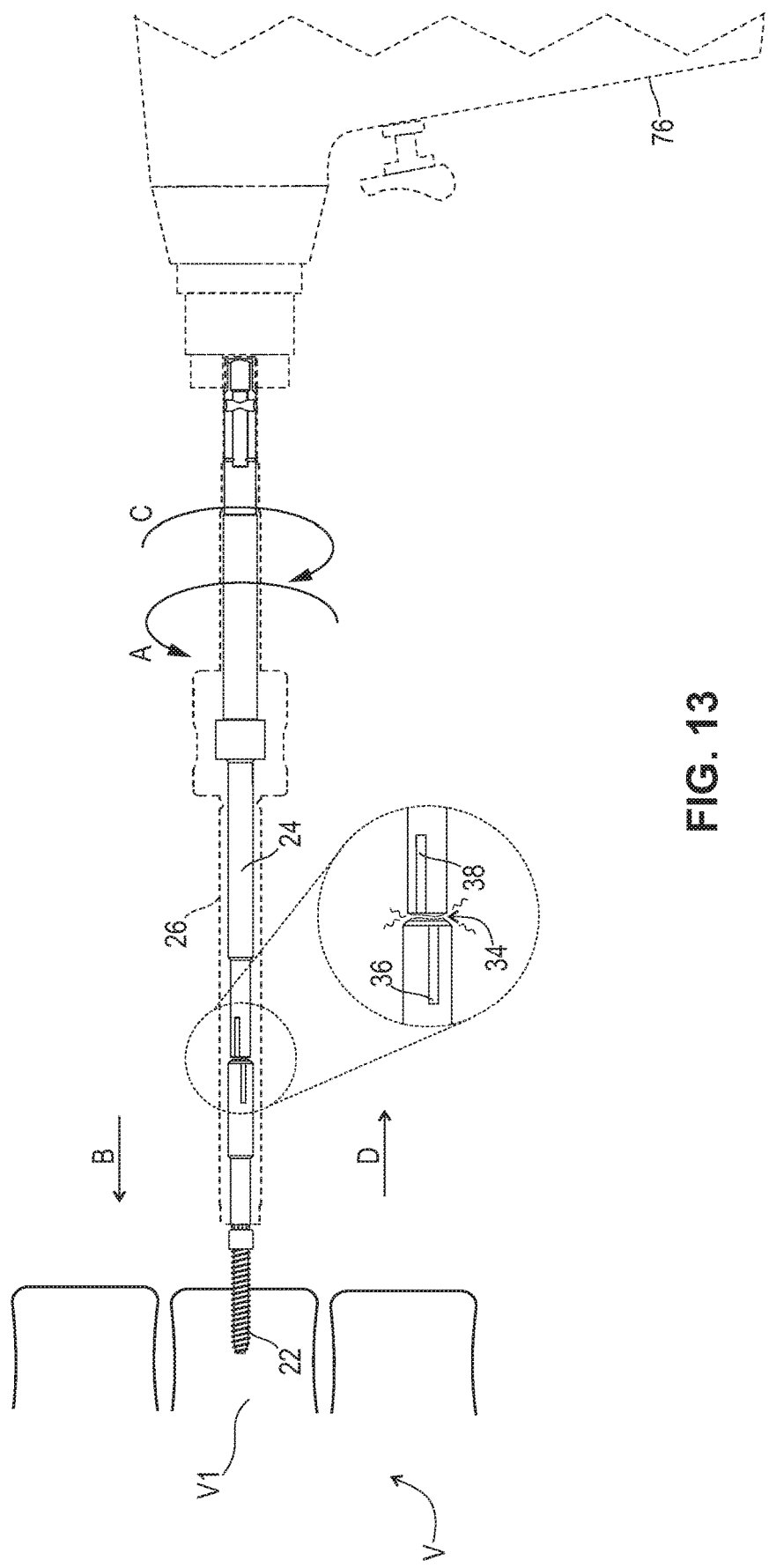
FIG. 13 is a partially phantom side view of the surgical instrument, such as the driver of FIG. 3 where the distal end of the driver is shown engaging a head of a bone fastener so as to implant the bone fastener at a surgical site, such as a vertebra V1.

The distal end of the elongated body and the distal end of the outer sleeve at the threaded portion engage the head of the bone fastener. The threaded portion of the outer sleeve pulls and/or draws the bone fastener axially into the cavity and into engagement with the distal end of the elongated body when the gripping portion is rotated in the direction of arrow A, as shown in FIGS. 10-13. The head of the bone fastener can be captured by the driver, and the driver can be connected to an oscillating tool, such as, for example, a surgical drill 76. The surgical drill fixedly engages with the proximal end of the elongated body. The surgical drill then rotates the elongated body at a certain torque in the direction of arrow A, and the bone fastener engages and advances in a distal direction, as shown by arrow B in FIGS. 12 and 13, and into a vertebra V1 for implantation. During implantation, if the torque reaches a predetermined torque of from about 18.5 to about 20 N-m, as described herein, the frangible region of the elongated body can either deform, as shown in FIG. 12 or break, as shown in FIG. 13.

If the frangible region starts to deform, the first visual indicia and the second visual indicia will not be in alignment and can be visually inspected by the user via the one or more windows of the outer sleeve. Once plastic deformation is confirmed by the user, the user can disengage the driver from the bone fastener and the surgical site. However, if plastic deformation is not seen by the user, the frangible region will break when the predetermined torque is reached, as shown in FIG. 13. Once the frangible region breaks, the distal end of the elongated body will remain attached to the head of the bone fastener. In particular, about 1 to about 3.5 inches of the elongated body of the driver will extend from the head of the bone fastener, depending on the location of the frangible region, and will extend from the surgical site. The fragmented section of the elongated body extending from the surgical site can be easily removed.

In some embodiments, when the driver is being used, if a torque value is reached that is greater than the ultimate torque for the driver, the driver will break where the frangible region is located. However, the piece(s) can easily be removed from the surgical site because the frangible region is spaced a convenient distance from the distal end of the driver that allows easy removal. This also prevents torque values that are greater than the ultimate torque being reached for the bone fastener and for other parts of the driver. Torque values greater than the ultimate torque for the bone fastener may cause the bone fastener to fragment and eventually fail over time.

It is to be understood by those of ordinary skill in the art that the frangible region is not required to break, fragment, tear or fracture during use of the driver and that the frangible region can remain intact if a predetermined torque is not reached. However, once the frangible region breaks, the driver can no longer be used. In some embodiments, to remove the bone fastener from vertebra V1, the gripping portion is rotated in the direction of arrow C to remove the bone fastener and the driver will move in a proximal direction, shown by arrow D in FIG. 13.

Upon completion of a procedure, the driver, additional surgical instruments and/or tools, assemblies and non-implanted components are removed and the incision(s) are closed.

The components of the bone fastener can be fabricated from biologically acceptable materials suitable for medical applications, including metals, synthetic polymers, ceramics and bone material and/or their composites. For example, the components of the driver and/or the bone fastener, individually or collectively, can be fabricated from materials such as steel, steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate and their combinations.

The components of the driver and/or bone fastener, individually or collectively, may also be fabricated from a heterogeneous material such as a combination of two or more of the above-described materials. The components of the driver and/or the bone fastener may be monolithically formed, integrally connected or include fastening elements and/or instruments, as described herein.

The driver and/or the bone fastener can be employed, for example, with a minimally invasive procedure, including percutaneous techniques, mini-open and open surgical techniques to deliver and introduce instrumentation and/or components of spinal constructs at a surgical site within a body of a patient, for example, a section of a spine. In some embodiments, one or more of the components of the driver are configured for engagement with existing spinal constructs, which may include spinal implants such as one or more rods, fasteners, plates and connectors. In some embodiments, the spinal constructs can be attached with vertebrae in a revision surgery to manipulate tissue and/or correct a spinal disorder, as described herein.

Methods of Use

In some embodiments, a method for implanting a bone fastener to a surgical site is provided. The method comprises providing a surgical instrument, the surgical instrument comprising an elongated body having a frangible region and a distal end adjacent to the frangible region, the distal end of the surgical instrument configured to engage the bone fastener, the bone fastener being less frangible than the frangible region of the elongated body of the surgical instrument; and engaging the distal end of the surgical instrument with the bone fastener so as to implant the bone fastener at the surgical site. It is to be understood that the surgical instrument is driver 20, as described above. In some embodiments, the bone fastener has at least a first frangible region, the first frangible region of the bone fastener being less frangible than the frangible region of the elongated body of the surgical instrument.

In some embodiments, the engaging further comprises rotating the bone fastener at a predetermined torque. In some embodiments, when the predetermined torque is from about 18.5 to about 20 Newton meter (N-m), the frangible region will break-off and about 1 to about 3.5 inches of the distal end of the elongated body will remain in a head of the bone fastener.

In some embodiments, the methods may use surgical instruments and/or bone fasteners that include radiomarkers for identification under x-ray, fluoroscopy, CT or other imaging techniques. In some embodiments, the use of surgical navigation, microsurgical and image guided technologies may be employed to access, view and repair spinal deterioration or damage, with the aid of the driver.

In some embodiments, the driver may be used in conjunction with one or a plurality of plates, connectors and/or bone fasteners for use with a single vertebral level or a plurality of vertebral levels, as described above.

In some embodiments, the driver may be used in conjunction with an agent, which may be disposed, packed, coated or layered within, on or about the components and/or surfaces of the bone fastener or other fixation elements, as described herein. In some embodiments, the agent may include bone growth promoting material, such as, for example, bone graft to enhance fixation of the fixation elements with vertebrae. In some embodiments, the agent may be HA coating. In some embodiments, the agent may include one or a plurality of therapeutic agents and/or pharmacological agents for release, including sustained release, to treat, for example, pain, inflammation and degeneration.

In some embodiments, the driver may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the driver of the present disclosure may be employed with other osteal and bone related applications, including those associated with diagnostics and therapeutics. In some embodiments, the driver may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The driver of the present disclosure may also be alternatively employed with procedures for treating the lumbar, cervical, thoracic, sacral and pelvic regions of a spinal column. The driver of the present disclosure may also be used on animals, bone models and other non-living substrates, such as, for example, in training, testing and demonstration.

Kits

A kit for implanting a bone fastener is provided. The kit comprising a surgical instrument for implanting a bone fastener, the surgical instrument comprising an elongated body having a frangible region and a distal end adjacent to the frangible region, the distal end of the surgical instrument configured to engage the bone fastener, the bone fastener being less frangible than the frangible region of the elongated body of the surgical instrument; and a bone fastener configured to engage the distal end of the surgical instrument. In various embodiments, the bone fastener has at least a first frangible region, the first frangible region of the bone fastener being less frangible than the frangible region of the elongated body of the surgical instrument. It is to be understood that the surgical instrument can be driver 20, as described above.

In some embodiments, the surgical instrument comprises a first visual indicia and a second visual indicia. The first visual indicia located on a first portion of the elongated body, adjacent to and contacting the frangible region of the elongated body, and the second visual indicia located on a second portion of the elongated body, adjacent to and also contacting the frangible region to align with the first visual indicia.

In various embodiments, a kit is provided comprising the surgical instrument, such as driver 20 and bone fastener 22. The kit may include additional parts or other components to be used to assist in the implantation of the bone fastener (e.g., additional fixation elements, wipes, needles, syringes, mixing devices, etc.). The kit may include the driver in a first compartment. The second compartment may include one or more bone fasteners. The third compartment may include a tray used for holding surgical tools and/or loading bone material into the bone fastener and/or the surgical site. The fourth compartment may include other instruments or additional fixation elements such as one or more plates needed for the implantation. A fifth compartment may include gloves, drapes, wound dressings and other procedural supplies for maintaining sterility of the implanting process, as well as an instruction booklet. A sixth compartment may include needles, additional devices and/or sutures. Each tool may be separately packaged in a plastic pouch that is sterilized. A seventh compartment may include an agent for radiographic imaging. A clear plastic cover may be placed over the compartments to maintain sterility.

In various embodiments, one or more components of the kit is sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

In various embodiments, gamma radiation is used in the terminal sterilization step, which involves utilizing ionizing energy from gamma rays that penetrate deeply into the components of the kit. Gamma rays are highly effective in killing microorganisms, they leave no residues, nor do they have sufficient energy to impart radioactivity to the apparatus. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the kit. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument for implanting a bone fastener, the surgical instrument comprising an elongated body having a frangible region disposed between a proximal end and a distal end of the elongated body, the distal end of the surgical instrument configured to engage the bone fastener, the bone fastener being less frangible than the frangible region of the elongated body of the surgical instrument, wherein the distal end of the surgical instrument comprises a tip comprising a second frangible region, the second frangible region being less frangible than the frangible region of the elongated body of the surgical instrument, and the surgical instrument comprises a first visual indicia and a second visual indicia, the first visual indicia located at a first portion of the elongated body, adjacent to or contacting the frangible region of the elongated body, and the second visual indicia located on a second portion of the elongated body, adjacent to or also contacting the frangible region so as to align with the first visual indicia such that the first visual indicia and the second visual indicia indicate plastic deformation at the frangible region when the first visual indicia and the second visual indicia are not aligned.

2. The surgical instrument of claim 1, wherein the bone fastener has at least a first frangible region, the first frangible region of the bone fastener being less frangible than the frangible region of the elongated body of the surgical instrument and the second frangible region of the surgical instrument is more frangible than the first frangible region of the bone fastener.

3. The surgical instrument of claim 2, wherein the frangible region of the surgical instrument, the first frangible region of the bone fastener or the second frangible region is located at the distal end of the elongated body and deforms at a predetermined torque.

4. The surgical instrument of claim 3, wherein the predetermined torque is from about 18.5 to about 20 Newton meter (N-m).

5. The surgical instrument of claim 1, wherein the frangible region is positioned from about 1 to about 3.5 inches from the distal end of the elongated body.

6. The surgical instrument of claim 1, wherein the frangible region comprises a shear ring.

7. The surgical instrument of claim 1, wherein the frangible region has a diameter that is less than a diameter of the distal end of the elongated body.

8. The surgical instrument of claim 1, wherein the first visual indicia and the second visual indicia comprise a laser marking.

9. The surgical instrument of claim 8, wherein the laser marking is linear.

10. The surgical instrument of claim 1, wherein the distal end of the surgical instrument engages a head of the bone fastener, the head of the bone fastener having at least a first frangible region.

11. The surgical instrument of claim 1, wherein the surgical instrument is a driver comprising the elongated body and an outer sleeve, the outer sleeve being movable relative to the elongated body to engage a head of the bone fastener.

12. The surgical instrument of claim 1, wherein the surgical instrument is a driver, a drill bit, or a burr.

13. The surgical instrument of claim 1, wherein the surgical instrument comprises stainless steel and the bone fastener is titanium.

14. A kit for implanting a bone fastener, the kit comprising a surgical instrument comprising an elongated body having a frangible region and a distal end adjacent to the frangible region, the distal end of the surgical instrument configured to engage the bone fastener, the bone fastener being less frangible than the frangible region of the elongated body of the surgical instrument; and the bone fastener configured to engage the distal end of the surgical instrument, wherein the distal end of the surgical instrument comprises a second frangible region, the second frangible region being less frangible than the frangible region of the elongated body of the surgical instrument and configured to deform at a predetermined torque, and the surgical instrument is a driver comprising the elongated body and an outer sleeve, the outer sleeve being movable relative to the elongated body to engage a head of the bone fastener.

15. The kit of claim 14, wherein (i) the bone fastener has at least a first frangible region, the first frangible region of the bone fastener being less frangible than the frangible region of the elongated body of the surgical instrument; or (ii) the surgical instrument comprises a first visual indicia and a second visual indicia, the first visual indicia located on a first portion of the elongated body, adjacent to or contacting the frangible region of the elongated body, and the second visual indicia located on a second portion of the elongated body, adjacent to or also contacting the frangible region so as to align with the first visual indicia.

16. A surgical instrument for implanting a bone fastener, the surgical instrument comprising an elongated body having a frangible region disposed between a proximal end and a distal of the elongated body, the distal end of the surgical instrument configured to engage the bone fastener, the bone fastener being less frangible than the frangible region of the elongated body of the surgical instrument, and the elongated body comprising a first visual indicia and a second visual indicia, the first visual indicia located at a first portion of the elongated body, adjacent to or contacting the frangible region of the elongated body, and the second visual indicia located on a second portion of the elongated body, adjacent to or also contacting the frangible region so as to align with the first visual indicia, wherein the distal end of the surgical instrument comprises a tip comprising a second frangible region, the second frangible region being less frangible than the frangible region of the elongated body of the surgical instrument, and the surgical instrument is a driver comprising the elongated body and an outer sleeve, the outer sleeve being movable relative to the elongated body to engage a head of the bone fastener.

\* \* \* \* \*